United States Patent
Ghufaili et al.

(10) Patent No.: US 12,421,850 B2
(45) Date of Patent: Sep. 23, 2025

(54) SYSTEM FOR PROVIDING REAL-TIME PREDICTIVE CARBON DIOXIDE CORROSION RATE MODELLING

(71) Applicant: SAUDI ARABIAN OIL COMPANY, Dhahran (SA)

(72) Inventors: Mohammad Ghufaili, Dammam (SA); Mohamud M. Farah, Ras Tanura (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 17/938,072

(22) Filed: Oct. 5, 2022

(65) Prior Publication Data

US 2024/0117736 A1    Apr. 11, 2024

(51) Int. Cl.
*C09K 8/54* (2006.01)
*E21B 49/08* (2006.01)
*G01N 33/24* (2006.01)

(52) U.S. Cl.
CPC .......... *E21B 49/0875* (2020.05); *C09K 8/54* (2013.01); *G01N 33/24* (2013.01)

(58) Field of Classification Search
CPC .................. C09K 8/24; C09K 8/145
See application file for complete search history.

(56) References Cited

U.S. PATENT DOCUMENTS

| | | | |
|---|---|---|---|
| 8,447,529 B2 * | 5/2013 | Hernandez | F17D 5/00 |
| | | | 205/777 |
| 9,317,635 B2 | 4/2016 | O'Connor et al. | |
| 11,034,418 B2 | 6/2021 | Lee | |
| 2022/0205353 A1 * | 6/2022 | Liu | E21B 47/006 |

FOREIGN PATENT DOCUMENTS

| | | |
|---|---|---|
| AU | 2021105665 A4 | 10/2021 |
| CN | 102305352 A | 1/2012 |
| CN | 111578150 A | 8/2020 |
| WO | 2022081533 A1 | 4/2022 |

OTHER PUBLICATIONS

Abbas, Muhammad Hashim. "Modelling CO2 corrosion of pipeline steels." (2016).

\* cited by examiner

*Primary Examiner* — Kumar R Bhushan
(74) *Attorney, Agent, or Firm* — Vorys, Sater, Seymour and Pease LLP

(57) ABSTRACT

A system and method for providing real-time predictive carbon dioxide ($CO_2$) corrosion rate modelling for an oil and gas operation facility includes a modeling system configured to receive dynamic process input data of the oil and gas operation facility, including data relating to $CO_2$ inhibitor residuals of the oil and gas operation facility. The modeling system implements a semi-empirical real-time corrosion rate model and an injection control module operable to control an injection rate of $CO_2$ inhibitor into a component of the oil and gas operation facility based on the semi-empirical real-time corrosion rate model.

12 Claims, 5 Drawing Sheets

SYSTEM FOR PROVIDING REAL-TIME PREDICTIVE CARBON DIOXIDE CORROSION RATE MODELLING

FIELD OF THE DISCLOSURE

The present disclosure relates generally to corrosion rate modeling, and, more particularly, to real-time carbon dioxide ($CO_2$) corrosion rate modelling for oil and gas operation facilities.

BACKGROUND OF THE DISCLOSURE

Carbon Steel (CS) materials are widely used across oil and gas production facilities and pipelines due to the lower capital expenditure relative to higher corrosion resistant alloys (CRAs). However, the multiphase nature of crude oil, containing a mixture of corrosive gases, liquid hydrocarbons and produced/formation water poses significant corrosion challenges, as CS is highly susceptible to a multitude of corrosion mechanisms such as carbon dioxide ($CO_2$), hydrogen sulfide ($H_2S$), under-deposit and microbial induced corrosion (MIC). Likewise, wet associated and non-associated gases pose a significant threat to CS material by virtue of the highly corrosive gases such as $CO_2$ and $H_2S$. Any ensuing corrosion will, over time, lead to progressive wall thickness deterioration, which can lead to loss of containment and major accident hazards (MAH) due to failure to withstand internal hoops stress. The negative implications associated with MAHs are severe due to deleterious health, safety, environmental and reputational implications.

$CO_2$ corrosion is one of the most prevalent corrosion mechanisms due to the high content of $CO_2$ in gas and oil production. Under the prevailing wet gasses and/or multiphase crude oil, the $CO_2$ reacts with the aqueous phase to form carbonic acid, which is highly corrosive to the CS material. Due to the ubiquitous nature of $CO_2$ corrosion in oil and gas production, predictive $CO_2$ corrosion rate plays a pivotal role during the design stage, where piping and equipment nominal thickness is determined by determining the corrosion allowance (CA) from the predicted corrosion rate. Other key decisions, both in design and operation, such as corrosion inhibition and overall design integrity management, are based on the predicted $CO_2$ corrosion rates.

$$CO_{2(g)} + H_2O_{(l)} \rightleftharpoons H_2CO_{3(aq.)}$$

$CO_2$ corrosion is affected by a number of parameters such as water chemistry, flow regime, pH, temperature, $CO_2$ partial pressure, scaling tendencies, contaminates such as volatile fatty acids (VFAs), ratio of other acid gases such as $H_2S$ and geometry and inclination of the piping.

A number of well-established empirical, semi-empirical and mechanistic $CO_2$ corrosion rate modelling mechanisms are available to those familiar with the corrosion art. The seminal De-Waard $CO_2$ empirical corrosion model has been pivotal in determining $CO_2$ corrosion rate. Other semi-empirical models are widely available and familiar to those in the art. Most of these models are currently excel-based, relying on process input that has been pre-recorded and/or offline. FIG. 1 diagrammatically illustrates the prior art process, which uses the following stipulated equation:

$$CRbase = f(T, pH) * fco2^{0.62} * \left(\frac{S}{19}\right)^{0.146 + 0.0324 fco2}$$

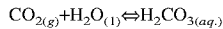

$$pH = 2.8686 + 0.7931 * \log_{10}(T) - 0.57 * \log_{10}(Pco2)$$

For Condensation: $pH = 2.8686 + 0.7931 * \log_{10}(T) - 0.57 * \log_{10}(Pco2)$ For Iron Saturated: $pH = 2.5907 + 0.8668 * \log_{10}(T) - 0.49 * \log_{10}(Pco2)$ For Higher Salinity: $pH = 2.7137 + 0.8002 * \log_{10}(T) - 0.57 * \log_{10}(Pco2)$ $$S = \frac{f * \rho_m * U_m^2}{2}$$

$$S = \frac{f * \rho_m * U_m^2}{2}$$

wherein,
fco2 = Fugacity of CO2,
S = Shear Stress (Pa),
T = Temperature (° F.),
P = Partial Pressure (psi),
f = Friction Factor,
$U_m$ = mixed superficial velocity (m/s), and $$\rho_m = \text{Mixed density}\left(\frac{\text{kg}}{m3}\right)$$

SUMMARY OF THE DISCLOSURE

Various details of the present disclosure are hereinafter summarized to provide a basic understanding. This summary is not an extensive overview of the disclosure and is neither intended to identify certain elements of the disclosure, nor to delineate the scope thereof. Rather, the primary purpose of this summary is to present some concepts of the disclosure in a simplified form prior to the more detailed description that is presented hereinafter.

According to an embodiment consistent with the present disclosure, a system for providing real-time predictive carbon dioxide ($CO_2$) corrosion rate modelling for an oil and gas operation facility includes a modeling system configured to receive dynamic process input data of the oil and gas operation facility, including data relating to $CO_2$ inhibitor residuals of the oil and gas operation facility. The modeling system implements a semi-empirical real-time corrosion rate model and an injection control module operable to control an injection rate of $CO_2$ inhibitor into a component of the oil and gas operation facility based on the semi-empirical real-time corrosion rate model.

In another embodiment, a method for providing real-time predictive carbon dioxide ($CO_2$) corrosion rate modelling for an oil and gas operation facility includes receiving dynamic process input data of the oil and gas operation facility, including data relating to $CO_2$ inhibitor residuals of the oil and gas operation facility, implementing a semi-empirical real-time corrosion rate model to the received dynamic process input data, and controlling an injection rate of $CO_2$ inhibitor into a component of the oil and gas operation facility based on the implemented semi-empirical real-time corrosion rate model.

Any combinations of the various embodiments and implementations disclosed herein can be used in a further embodiment, consistent with the disclosure. These and other aspects and features can be appreciated from the following description of certain embodiments presented herein in accordance with the disclosure and the accompanying drawings and claims.

DETAILED DESCRIPTION

Figure 1:
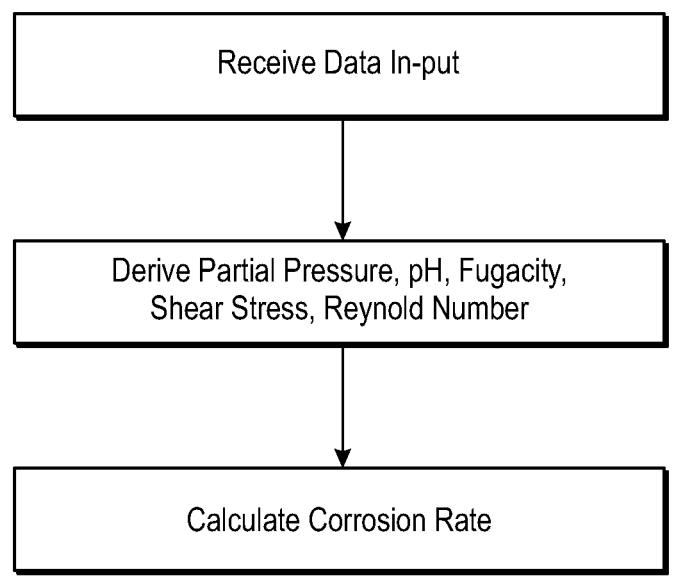
FIG. 1 is a flow diagram of a conventional method of calculating corrosion rate.

Embodiments of the present disclosure will now be described in detail with reference to the accompanying Figures. Like elements in the various figures may be denoted by like reference numerals for consistency. Further, in the following detailed description of embodiments of the present disclosure, numerous specific details are set forth in order to provide a more thorough understanding of the claimed subject matter. However, it will be apparent to one of ordinary skill in the art that the embodiments disclosed herein may be practiced without these specific details. In other instances, well-known features have not been described in detail to avoid unnecessarily complicating the description. Additionally, it will be apparent to one of ordinary skill in the art that the scale of the elements presented in the accompanying Figures may vary without departing from the scope of the present disclosure.

Embodiments in accordance with the present disclosure generally relate to . . . corrosion rate modeling, and, more particularly, to real-time carbon dioxide ($CO_2$) corrosion rate modelling for oil and gas operation facilities.

Figure 2:
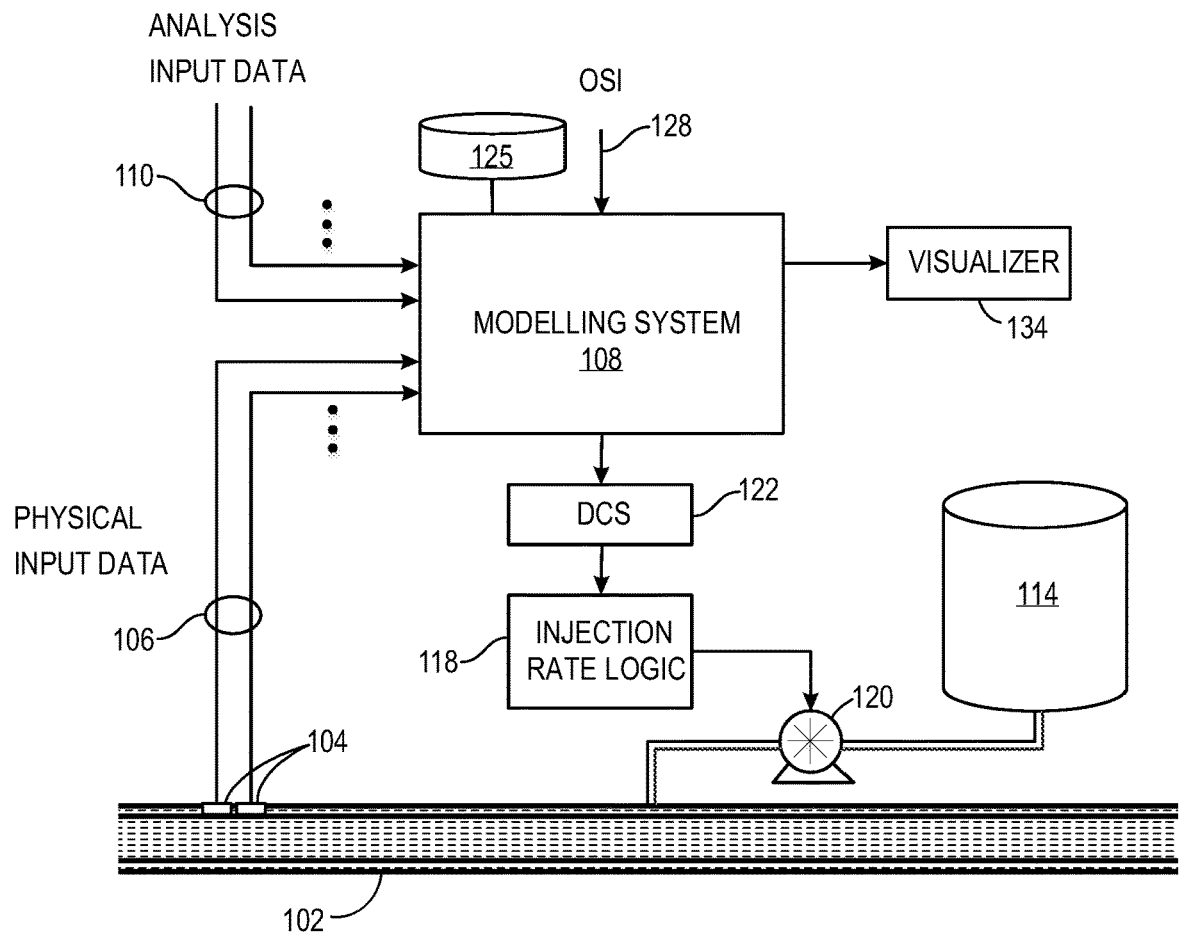
FIG. 2 is a schematic diagram of a system for providing real-time predictive carbon dioxide ($CO_2$) corrosion rate modelling in accordance with certain embodiments.

FIG. 2 is a schematic diagram of a system 100 for providing real-time predictive carbon dioxide ($CO_2$) corrosion rate modelling in accordance with certain embodiments. System 100 can be used to provide real-time $CO_2$ corrosion rate modelling for oil and gas operation facilities using dynamic process input data. One or more components of an oil and gas operation facility, such as a pipe 102, and/or other components such as a vessel, tank or the like (not shown), are monitored in operation and in real-time by sensors/field transmitters 104 that provide indicators of physical conditions relating to the component(s) and/or the contents of the component(s). Included among these physical conditions are pressure, temperature and flow rate, for instance. Component contents may be materials such as oil or natural gas, chemicals, additives, products or by-products, waste material, or any other materials associated with oil and gas operation facilities or carbon dioxide capture and storage facilities for instance. In the instant example, the material is oil, although other materials are contemplated.

Figure 3:
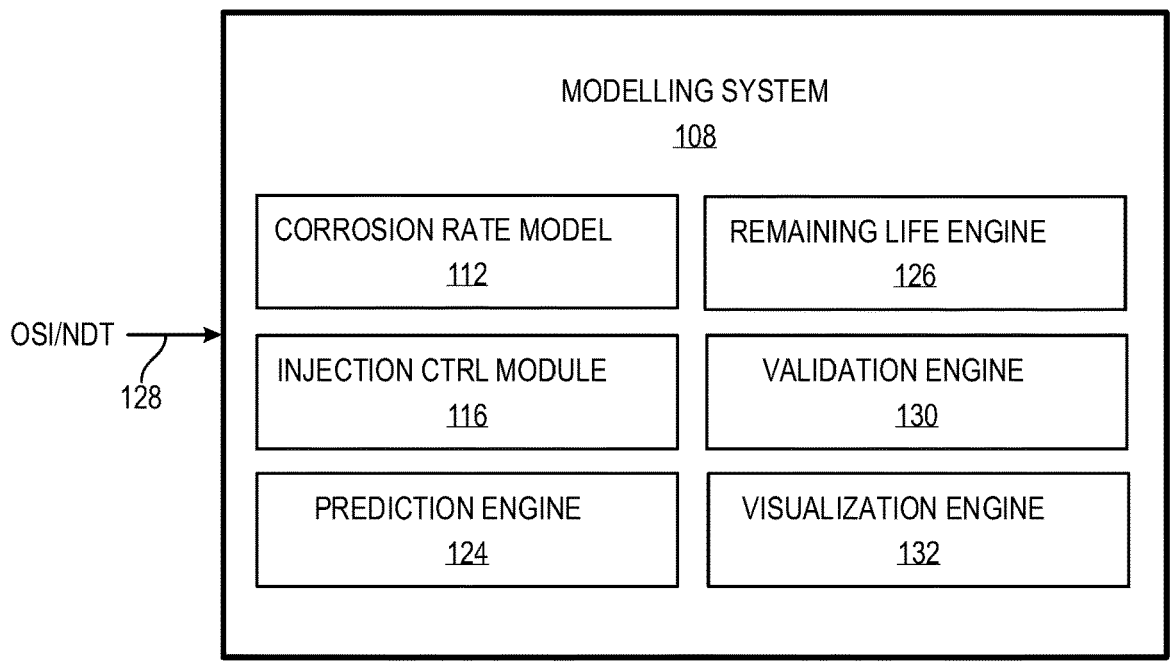
FIG. 3 is a block diagram of a modeling system in accordance with certain embodiments.

The indicators from sensors 104 are provided as real-time physical input data 106 to a modeling system 108, shown in more detail in FIG. 3. In certain embodiments, in addition to the real-time physical input data 106, analysis input data 110 can also be provided to modeling system 108. Analysis input data can be laboratory data that relate to for instance water chemistry, real-time residual corrosion inhibitor water chemistry analysis, molar composition, and pH, can be obtained through laboratory analysis of the contents of pipe 102 or other component. The real-time physical input data 106 and the analysis input data 110 may be collectively referred to as dynamic process input data. In one example, as mentioned above, the dynamic process input data relate to one or more of pressure, temperature, acid gases composition, water content, flow rate, pipe diameter, pipe wall thickness, and so on, pertaining to the component and/or its material contents.

Modeling system 108 implements a semi-empirical $CO_2$ corrosion rate model 112 (FIG. 3) whose input parameters include the dynamic process input data—that is, the real-time physical input data 106 and the analysis input data 110. In certain embodiments, the semi-empirical real-time corrosion rate model 112 can for instance be derived from the De-Waard model, but modified to have a higher and wider temperature range (5-150° C.), thereby taking larger account for the effect of protective corrosion films at high temperature and high pH than other models.

Modeling system 108 provides real-time $CO_2$ corrosion modelling and automated process control. It automates and optimizes the injection rate of corrosion inhibitor stored in tank 114 as a function of such factors as corrosion residuals based on inhibitor water chemistry analysis, and $CO_2$ corrosion rate determined by the model 112. An injection control module 116 of modeling system 108 provides control parameters to injection rate logic 118—for example a programmable circuit—operable to issue command signals to pump 120 to thereby selectively increase or decrease the inhibitor injection rate into pipe 102 as necessary to minimize corrosion in the oil and gas system component(s) and to thereby increase the piping components remaining life for instance, and to hence contribute to continuing asset integrity and to preventing loss of primary containment (LOPC) resulting from CO2 corrosion. In certain embodiments, injection rate logic 118 and pump 120 rely on automated Electronic Capacity Control (ECC) chemical injection pump technology that is capable of receiving remote signals for controlling pump discharge rates to lower the observed online $CO_2$ corrosion rate. A plant's distributed control system (DCS) 122 may be part of the control mechanism and operative to receive and issue control signals as described herein.

In certain embodiments, modeling system 108 includes a prediction engine 124 and a remaining life engine 126 that are respectively operable to make determinations of predicted corrosion rate and remaining life for components as such as pipe 102, or other pipes or vessels. This can be performed in conjunction with on-stream inspection (OSI) data 128 received by modeling system 108. OSI data 128 can include for example Advanced Non-Destructive Testing (NDT) such as Ultrasonic Testing (UT) and can be received and deployed in real-time, or it can be stored in and accessed from a database 125 by modeling system 108, or a combination of these expedients. OSI can include dynamic inspection data such as pipe wall thickness, pipe diameter, and corrosion circuits for instance. In certain embodiments, the determinations of predicted corrosion rate and remaining life can be based on a model that takes into account historical corrosion rate data. Such historical data and/or OSI data 128 can be stored in and accessed from a database 125 by modeling system 108.

Figure 4:
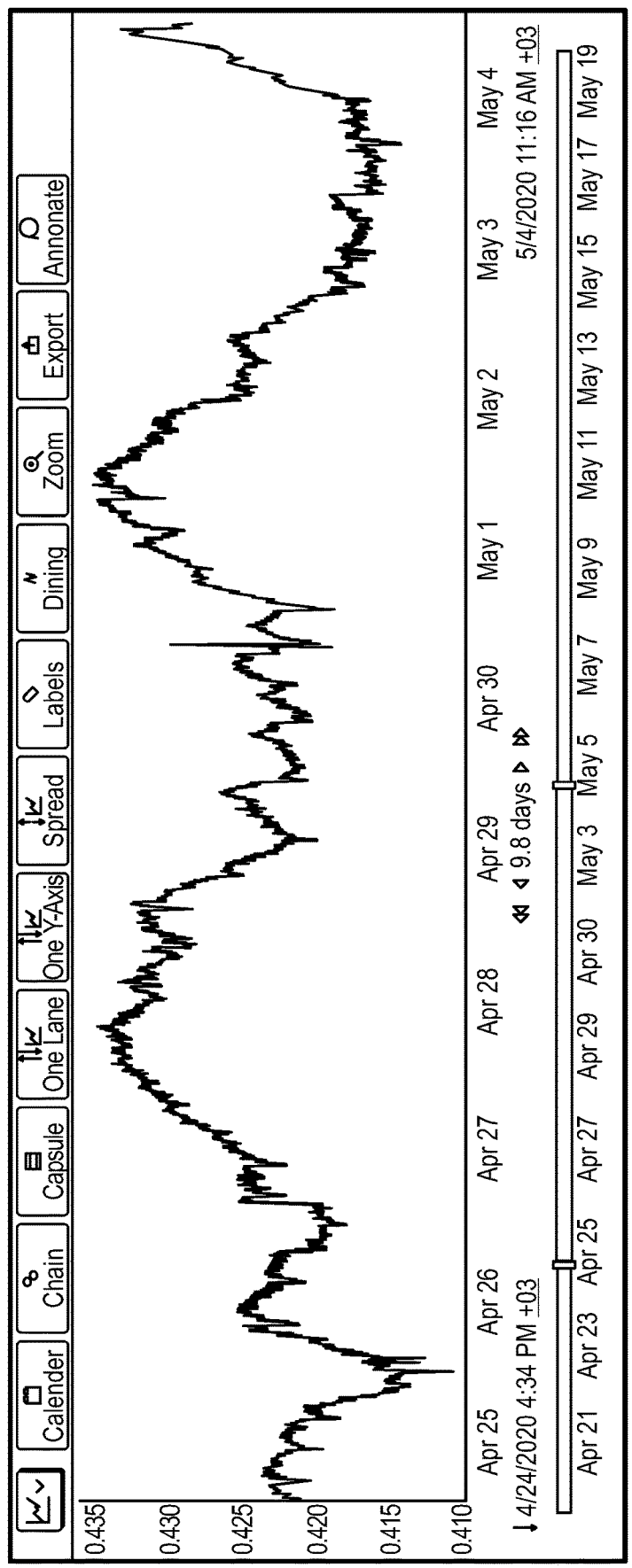
FIG. 4 is an example of a graphic visualization of corrosion rate plotted over time in daily increments in accordance with certain embodiments.

In certain embodiments, a validation engine 130 can be provided to ascertain the predicted corrosion rate and remaining life by conducting extensive NDT inspection whose information can be included in the OSI data 128 and deployed in real-time or retrieved from database 125. In addition, modeling system 108 can include a visualization engine 132 operable to provide a visualization of the real-time corrosion rate, using a visualizer 134, based on corrosion rate model 112. An example of such a visualization is shown in FIG. 4, wherein corrosion rate is plotted over time in daily increments.

Figure 5:
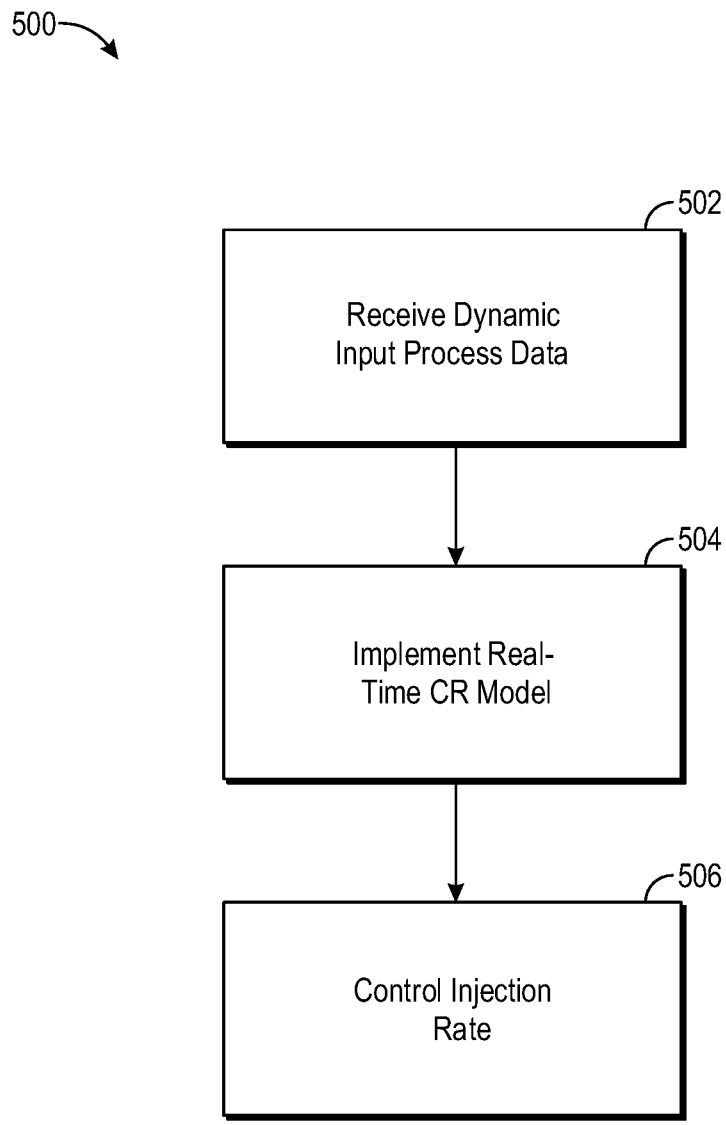
FIG. 5 is a flow diagram of a method for providing real-time predictive carbon dioxide ($CO_2$) corrosion rate modelling for an oil and gas operation facility in accordance with certain embodiments.

In view of the foregoing structural and functional features described above, an example method will be better appreciated with reference to FIG. 5. While, for purposes of simplicity of explanation, the example method of FIG. 5 is shown and described as executing serially, it is to be understood and appreciated that the present examples are not limited by the illustrated order, as some actions could in other examples occur in different orders, multiple times and/or concurrently from that shown and described herein. Moreover, it is not necessary that all described actions be performed to implement the methods.

FIG. 5 is an example of a method 500 for providing real-time predictive carbon dioxide ($CO_2$) corrosion rate modelling for an oil and gas operation facility in accordance with certain embodiments. The method 500 can be implemented by a modeling system as shown in FIGS. 2 and 3. The method 500 can begin at 502 by receiving dynamic process input data of the oil and gas operation facility, including data relating to $CO_2$ inhibitor residuals of the oil and gas operation facility. At 504, a semi-empirical real-time corrosion rate model is applied to the received dynamic process input data, and at 506, an injection rate of $CO_2$ inhibitor into a component of the oil and gas operation facility is selectively controlled based on the implemented semi-empirical real-time corrosion rate model.

In view of the foregoing structural and functional description, those skilled in the art will appreciate that portions of the embodiments may be embodied as a method, data processing system, or computer program product. Accordingly, these portions of the present embodiments may take the form of an entirely hardware embodiment, an entirely software embodiment, or an embodiment combining software and hardware, such as shown and described with respect to the computer system of FIG. 6. Furthermore, portions of the embodiments may be a computer program product on a computer-usable storage medium having computer readable program code on the medium. Any non-transitory, tangible storage media possessing structure may be utilized including, but not limited to, static and dynamic storage devices, hard disks, optical storage devices, and magnetic storage devices, but excludes any medium that is not eligible for patent protection under 35 U.S.C. § 101 (such as a propagating electrical or electromagnetic signal per se). As an example and not by way of limitation, a computer-readable storage media may include a semiconductor-based circuit or device or other IC (such, as for example, a field-programmable gate array (FPGA) or an ASIC), a hard disk, an HDD, a hybrid hard drive (HHD), an optical disc, an optical disc drive (ODD), a magneto-optical disc, a magneto-optical drive, a floppy disk, a floppy disk drive (FDD), magnetic tape, a holographic storage medium, a solid-state drive (SSD), a RAM-drive, a SECURE DIGITAL card, a SECURE DIGITAL drive, or another suitable computer-readable storage medium or a combination of two or more of these, where appropriate. A computer-readable non-transitory storage medium may be volatile, nonvolatile, or a combination of volatile and non-volatile, where appropriate.

Certain embodiments have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Figure 6:
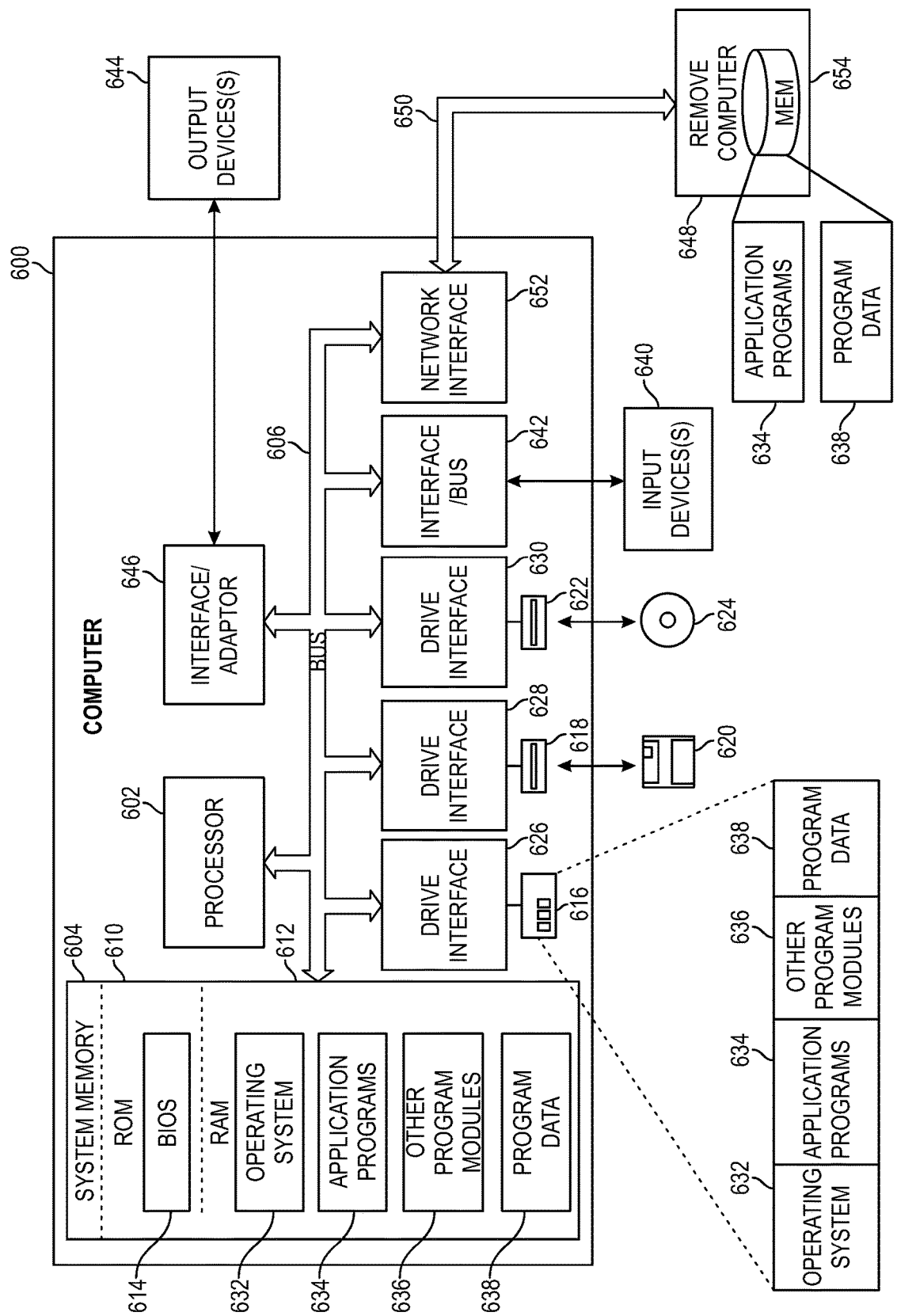
FIG. 6 is a block diagram of a computer system that can be employed to execute a system for providing real-time predictive carbon dioxide ($CO_2$) corrosion rate modelling in accordance with certain embodiments.

In this regard, FIG. 6 illustrates one example of a computer system 600 that can be employed to execute one or more embodiments of the present disclosure. Computer system 600 can be implemented on one or more general purpose networked computer systems, embedded computer systems, routers, switches, server devices, client devices, various intermediate devices/nodes or standalone computer systems. Additionally, computer system 6W) can be implemented on various mobile clients such as, for example, a personal digital assistant (PDA), laptop computer, pager, and the like, provided it includes sufficient processing capabilities.

Computer system 600 includes processing unit 602, system memory 604, and system bus 606 that couples various system components, including the system memory 604, to processing unit 602. Dual microprocessors and other multi-processor architectures also can be used as processing unit 602. System bus 606 may be any of several types of bus structure including a memory bus or memory controller, a peripheral bus, and a local bus using any of a variety of bus architectures. System memory 604 includes read only memory (ROM) 610 and random access memory (RAM) 612. A basic input/output system (BIOS) 614 can reside in ROM 610 containing the basic routines that help to transfer information among elements within computer system 600.

Computer system 600 can include a hard disk drive 616, magnetic disk drive 618. e.g., to read from or write to removable disk 620, and an optical disk drive 622. e.g., for reading CD-ROM disk 624 or to read from or write to other optical media. I-lard disk drive 616, magnetic disk drive 618, and optical disk drive 622 are connected to system bus 606 by a hard disk drive interface 626, a magnetic disk drive interface 628, and an optical drive interface 630, respectively. The drives and associated computer-readable media provide nonvolatile storage of data, data structures, and computer-executable instructions for computer system 600. Although the description of computer-readable media above refers to a hard disk, a removable magnetic disk and a CD, other types of media that are readable by a computer, such as magnetic cassettes, flash memory cards, digital video disks and the like, in a variety of forms, may also be used in the operating environment: further, any such media may contain computer-executable instructions for implementing one or more parts of embodiments shown and described herein.

A number of program modules may be stored in drives and RAM 610, including operating system 632, one or more application programs 634, other program modules 636, and program data 638. In some examples, the application programs 634 can include corrosion rate model 112, injection control module 116, prediction engine 124, remaining life engine 126, validation engine 130 and visualization engine 132, and the program data 638 can include historical corrosion rate data used in determinations of predicted corrosion rate and remaining life for instance. The application programs 634 and program data 638 can include functions and methods programmed to implement a semi-empirical $CO_2$ corrosion rate model 112 or other components, such as shown and described herein.

A user may enter commands and information into computer system 600 through one or more input devices 640, such as a pointing device (e.g., a mouse, touch screen), keyboard, microphone, joystick, game pad, scanner, and the like. These and other input devices 640 are often connected to processing unit 602 through a corresponding port interface 642 that is coupled to the system bus, but may be connected by other interfaces, such as a parallel port, serial port, or universal serial bus (USB). One or more output devices 644 (e.g., display, a monitor, printer, projector, or other type of displaying device) is also connected to system bus 606 via interface 646, such as a video adapter.

Computer system 600 may operate in a networked environment using logical connections to one or more remote computers, such as remote computer 648. Remote computer 648 may be a workstation, computer system, router, peer device, or other common network node, and typically includes many or all the elements described relative to computer system 600. The logical connections, schematically indicated at 650, can include a local area network (LAN) and a wide area network (WAN). When used in a LAN networking environment, computer system 600 can be connected to the local network through a network interface or adapter 652. When used in a WAN networking environment, computer system 600 can include a modem, or can be connected to a communications server on the LAN. The modem, which may be internal or external, can be connected to system bus 606 via an appropriate port interface. In a networked environment, application programs 634 or program data 638 depicted relative to computer system 300, or portions thereof, may be stored in a remote memory storage device 654.

Embodiments disclosed herein include:

A. A system for providing real-time predictive carbon dioxide ($CO_2$) corrosion rate modelling for an oil and gas operation facility includes a modeling system configured to receive dynamic process input data of the oil and gas operation facility, including data relating to $CO_2$ inhibitor residuals of the oil and gas operation facility. The modeling system implements a semi-empirical real-time corrosion rate model and an injection control module operable to control an injection rate of $CO_2$ inhibitor into a component of the oil and gas operation facility based on the semi-empirical real-time corrosion rate model.

B. A method for providing real-time predictive carbon dioxide ($CO_2$) corrosion rate modelling for an oil and gas operation facility includes receiving dynamic process input data of the oil and gas operation facility, including data relating to $CO_2$ inhibitor residuals of the oil and gas operation facility, implementing a semi-empirical real-time corrosion rate model to the received dynamic process input data, and controlling an injection rate of $CO_2$ inhibitor into a component of the oil and gas operation facility based on the implemented semi-empirical real-time corrosion rate model.

Each of embodiments A and B may have one or more of the following additional elements in any combination: Element 1: the dynamic process input data includes one or more of temperature, pressure, real-time residual corrosion inhibitor water chemistry, and acid gases composition. Element 2: the modeling system further includes a prediction engine operable to determine a predicted corrosion rate of a component of the oil and gas operation facility. Element 3: the prediction engine is operable to receive on-stream inspection (OSI) data and to determine the predicted corrosion rate based on said OSI data. Element 4: the modeling system further includes a remaining life engine operable to determine remaining life of a component of the oil and gas operation facility. Element 5: the remaining life engine is operable to receive on-stream inspection (OSI) data and to determine remaining life based on said OSI data. Element 6: the modeling system further includes a visualization engine operable to visualize a corrosion rate of the oil and gas operation facility. Element 7: further including a $CO_2$ inhibitor injection pump operable to controllably inject $CO_2$ inhibitor into a component of the oil and gas operation facility, wherein the modeling system further includes an injection control module and a programmable circuit for receiving control parameters from the injection control module and for issuing command signals to the $CO_2$ inhibitor injection pump to thereby controllably inject $CO_2$ inhibitor into a component of the oil and gas operation facility. Element 8: the dynamic process input data includes one or more of temperature, pressure, real-time residual corrosion inhibitor water chemistry, and acid gases composition. Element 9: further comprising determining a predicted corrosion rate of a component of the oil and gas operation facility. Element 10: further comprising receiving on-stream inspection (OSI) data and determining the predicted corrosion rate based on said OSI data. Element 11: further comprising determining remaining life of a component of the oil and gas operation facility. Element 12: further comprising receiving on-stream inspection (OSI) data and determining the remaining life based on said OSI data. Element 13: further comprising visualizing a corrosion rate of the oil and gas operation facility.

By way of non-limiting example, exemplary combinations applicable to A and B include: Element 2 with Element 3; Element 2 with Element 4; Element 3 with Element 5; Element 3 with Element 6; Element 5 with Element 7; Element 3 with Element 7; Element 3 with Element 8; Element 7 with Element 8; and Element 3 with Element 8.

The terminology used herein is for the purpose of describing particular embodiments only and is not intended to be limiting of the invention. As used herein, for example, the singular forms "a," "an," and "the" are intended to include the plural forms as well, unless the context clearly indicates otherwise. It will be further understood that the terms "contains", "containing", "includes", "including," "comprises", and/or "comprising," and variations thereof, when used in this specification, specify the presence of stated features, integers, steps, operations, elements, and/or components, but do not preclude the presence or addition of one or more other features, integers, steps, operations, elements, components, and/or groups thereof.

Any terms of orientation are used herein merely for purposes of convention and referencing and are not to be construed as limiting. However, it is recognized these terms could be used with reference to an operator or user. Accordingly, no limitations are implied or to be inferred. In addition, the use of ordinal numbers (e.g., first, second, third, etc.) is for distinction and not counting. For example, the use of "third" does not imply there must be a corresponding "first" or "second." Also, if used herein, the terms "coupled" or "coupled to" or "connected" or "connected to" or "attached" or "attached to" may indicate establishing either a direct or indirect connection, and is not limited to either unless expressly referenced as such. While the disclosure has described several exemplary embodiments, it will be understood by those skilled in the art that various changes can be made, and equivalents can be substituted for elements thereof, without departing from the spirit and scope of the invention. In addition, many modifications will be appreciated by those skilled in the art to adapt a particular instrument, situation, or material to embodiments of the disclosure without departing from the essential scope thereof. Therefore, it is intended that the invention not be limited to the particular embodiments disclosed, or to the best mode contemplated for carrying out this invention, but that the invention will include all embodiments falling within the scope of the appended claims. Moreover, reference in the appended claims to an apparatus or system or a component of an apparatus or system being adapted to, arranged to, capable of, configured to, enabled to, operable to, or operative to perform a particular function encompasses that apparatus, system, or component, whether or not it or that particular function is activated, turned on, or unlocked, as long as that apparatus, system, or component is so adapted, arranged, capable, configured, enabled, operable, or operative.

The invention claimed is:

1. A system for providing real-time predictive carbon dioxide (CO2) corrosion rate modelling for an oil and gas operation facility comprising:
    a modeling system configured to receive dynamic process input data of the oil and gas operation facility, including data relating to CO2 inhibitor residuals of the oil and gas operation facility, the modeling system including:
        a semi-empirical real-time corrosion rate model configured to provide real-time CO2 corrosion modelling and automated process control; and
        an injection control module operable to control an injection rate of CO2 inhibitor into a component of the oil and gas operation facility from a first injection rate to a second injection rate based on the semi-empirical real-time corrosion rate model.

2. The system of claim 1, wherein the dynamic process input data includes one or more of temperature, pressure, real-time residual corrosion inhibitor water chemistry, or acid gases composition.

3. The system of claim 1, wherein the modeling system further includes a prediction engine operable to determine a predicted corrosion rate of a component of the oil and gas operation facility.

4. The system of claim 3, wherein the prediction engine is operable to receive on-stream inspection (OSI) data and to determine the predicted corrosion rate based on said OSI data.

5. The system of claim 1, wherein the modeling system further includes a remaining life engine operable to determine remaining life of a component of the oil and gas operation facility.

6. The system of claim 5, wherein the remaining life engine is operable to receive on-stream inspection (OSI) data and to determine remaining life based on said OSI data.

7. The system of claim 1, wherein the modeling system further includes a visualization engine operable to visualize a corrosion rate of the oil and gas operation facility.

8. The system of claim 1, further including a CO2 inhibitor injection pump operable to controllably inject CO2 inhibitor into a component of the oil and gas operation facility, wherein the modeling system further includes an injection control module and a programmable circuit for receiving control parameters from the injection control module and for issuing command signals to the CO2 inhibitor injection pump to thereby controllably inject CO2 inhibitor into a component of the oil and gas operation facility.

9. The system of claim 1, wherein the dynamic process input data includes a temperature.

10. The system of claim 1, wherein the dynamic process input data includes a pressure.

11. The system of claim 1, wherein the dynamic process input data includes a real-time residual corrosion inhibitor water chemistry.

12. The system of claim 1, wherein the dynamic process input data includes an acid gases composition.

* * * * *